United States Patent [19]

Weber et al.

[11] 4,288,643

[45] Sep. 8, 1981

[54] PROCESS FOR PREPARING 2,3-DIMETHYL-BUTENE-2

[75] Inventors: Jürgen Weber, Oberhausen; Wolfgang Bernhagen, Mulheim an der Ruhr; Helmut Springer, Oberhausen, all of Fed. Rep. of Germany

[73] Assignee: Ruhrchemie Aktiengesellschaft, Oberhausen, Fed. Rep. of Germany

[21] Appl. No.: 146,830

[22] Filed: May 5, 1980

[30] Foreign Application Priority Data

May 3, 1979 [DE] Fed. Rep. of Germany ....... 2917779

[51] Int. Cl.³ ............................................. C07C 1/253
[52] U.S. Cl. .................................. 585/324; 585/639; 585/664; 585/668
[58] Field of Search ................ 585/324, 639, 664, 668

[56] References Cited

U.S. PATENT DOCUMENTS

| 3,247,277 | 4/1966 | Kruse et al. | 585/324 |
| 3,723,562 | 3/1973 | Heckelsberg | 585/324 |
| 3,758,610 | 9/1973 | Turner | 585/324 |

Primary Examiner—Curtis R. Davis
Attorney, Agent, or Firm—Bierman & Bierman

[57] ABSTRACT

A process for the preparation of 2,3-dimethylbutene-2 is disclosed, which comprises the steps of converting isovaleraldehyde to isopropylacrolein, hydrogenating α-isopropylacrolein to form 2,3-dimethylbutanol, dehydrating 2,3-dimethylbutanol to form an olefin mixture comprising 2,3-dimethylbutene-1 and 2,3-dimethylbutene-2, and isomerizing the 2,3-dimethylbutene-1 contained in the mixture into 2,3-dimethylbutene-2. The present process is technically simple and inexpensive to utilize, and results in high yields of the desired product.

19 Claims, No Drawings

PROCESS FOR PREPARING 2,3-DIMETHYL-BUTENE-2

This application claims the priority of German patent application Ser. No. P 29 17 779.5, filed May 3, 1979.

The present invention relates to a process for preparing 2,3-dimethylbutene-2.

The compound 2,3-dimethylbutene-2 has importance as an intermediate for organic syntheses. For example, it may be converted with hydrogen peroxide to form pinnacol, or may be dehydrogenated to form 2,3-dimethyl-1,3-butadiene.

The preparation of 2,3-dimethylbutene-2 by catalytic dimerization of propylene is known. The catalysts utilized in this known preparation are organo metallic compounds of nickel, thorium, cerium or aluminum. Depending on the catalyst system employed, methyl pentenes, 2,3-dimethylbutene-1 and 2,3-dimethylbutene-2, as well as other isomers of $C_6$ olefins are preferentially formed in varying amounts. Additionally, further by-products of this reaction include trimers and tetramers, as well as higher oligomers of propylene.

In the selective dimerization of propylene to form 2,3-dimethylbutene, mixtures of both possible isomers are always formed, since thermodynamic equilibrium which almost completely favors the formation of 2,3-dimethylbutene-2, is not established. The ratio in which the two isomers are formed depends upon the catalyst system and the chosen reaction conditions. In order to carry out the dimerization selectively to favor the formation of 2,3-dimethylbutene-2, reaction conditions must be established and maintained that can only be achieved at great expense of energy, time and effort. Thus U.S. Pat. Nos. 3,622,649 and 3,482,001 recommend the adjustment of the reaction temperature to below 25° C., and, in particular, to between 0° and 10° C., in order to favor the formation of 2,3-dimethylbutene-2.

In addition, certain problems exist in connection with the further processing of the reaction mixture. Thus, although the two isomeric 2,3-dimethylbutenes can be separated without great effort on the basis of the difference in their boiling points of approximately 18° C., the distillative separation of the methylpentenes also present in the mixture after the isomerization of propylene, is difficult. The boiling points of the isomeric methylpentenes and the isomeric 2,3-dimethylbutenes are so close together that an economic separation of the olefin mixture is impossible.

Certain alternate syntheses of 2,3-dimethylbutene-2 are known, which comprise the dehydrogenation of 2,3-dimethylbutane and the partial hydrogenation of 2,3-dimethylbutadiene. Both starting substances are, however, difficult to obtain, and the corresponding processes are therefore used industrially only in exceptional cases.

Having regard to the afore-mentioned difficulties in preparing 2,3-dimethylbutene-2, there therefore existed the task of developing a process which does not have the afore-described disadvantages and will enable dimethylbutene to be produced in high yields in a technically simple manner.

In accordance with the invention, 2,3-dimethylbutene-2 is prepared by methylenating isovaleraldehyde to form α-isopropylacrolein, hydrogenating α-isopropylacrolein to 2,3-dimethylbutanol, dehydrating 2,3-dimethylbutanol to form a mixture of the isomeric olefins 2,3-dimethylbutene-1 and 2,3-dimethylbutene-2, and isomerizing the 2,3-dimethylbutene-1 contained in the olefin mixture into 2,3-dimethylbutene-2.

No special purity requirements are placed on the isovaleraldehyde used as the starting substance. Accordingly, industrial isovaleraldehyde may be utilized, which can be prepared by one of several known methods, such as the hydroformylation of isobutene.

The introduction of the methylene group into the α-position of isovaleraldehyde may be accomplished by one of several methods known per se for aldehydes. Thus, isovaleraldehyde can be condensed by the Mannich reaction with stoichiometric amounts of a primary or secondary amine, and formaldehyde. Preferably, isovaleraldehyde may be mixed with a 30% aqueous solution of formaldehyde, and the mixture may be heated in the presence of catalytic amounts of a secondary amine having the general formula

$$R_1CH_2-CH_2-NH-R_2$$

wherein $R_1$ is selected from hydrogen, alkyl radicals having up to 11 carbon atoms, and cycloaliphatic radicals having 5 or 6 carbon atoms, and $R_2$ is selected from alkyl radicals having up to 13 carbon atoms, and cycloaliphatic radicals having 5 to 6 carbon atoms. A particularly preferred secondary amine comprises di-n-butylamine.

The condensation of isovaleraldehyde in the presence of formaldehyde and the secondary amine catalyst, proceeds by the heating of the mixture in a pressurized reactor at temperatures ranging from 60° to 120° C., under the ambient pressure developed within the reactor under these conditions. For example, ambient internal pressure may range on the order of 1.6 to 1.8 atmospheres, or higher, depending of course upon the exact proportions of ingredients, reactor size and reaction temperature employed. The foregoing conditions are naturally exemplary only, and are not intended to limit the scope of the invention.

The performance of the above condensation reaction under the specified conditions results in a yield of about 90% α-isopropylacrolein having a purity of greater than 99%. Additional purification operations, such as fractional distillation, are accordingly unnecessary, and it is sufficient to distill off the reaction product from the higher boiling point fractions also present.

The conversion of α-isopropylacrolein to 2,3-dimethylbutanol-1 can be accomplished by catalytic hydrogenation, in which hydrogen is taken up by the acrolein in either a 1-stage or a 2-stage reaction. In the 1-stage hydrogenation, the carbonyl group and the double bond are simultaneously reacted with hydrogen and the saturated alcohol is obtained directly from the unsaturated aldehyde. This form of hydrogenation of α-isopropylacrolein may be conveniently carried out in the liquid phase in the presence of a diluent selected from hydrocarbons such as cyclohexane, and alcohols such as 2-ethylhexanol or the desired product, 2,3-dimethylbutanol. A nickel catalyst is employed in this reaction, and preferably contains 20 to 100% by weight of nickel. The catalyst utilizes a catalyst support which is preferably selected from kieselguhr and aluminum oxide. The 1-stage reaction is conducted at a temperature ranging from 90° to 160° C., and under pressure ranging from 50 to 150 atmospheres. Depending upon the nickel content of the catalyst, it may be utilized in an amount ranging from 2 to 15% by weight of α-isopropylacrolein.

In the 2-stage hydrogenation reaction, the α-isopropylacrolein is first converted to the corresponding saturated aldehyde, 2,3-dimethylbutanal. The catalysts utilized in this reaction comprise nobel metal catalysts, such as palladium catalysts. These catalysts are utilized in amounts ranging from 0.1 to 2% by weight, and preferably 1% by weight of the unsaturated aldehyde. The reaction proceeds at temperatures of from about 80° to about 130° C., and preferably from 90° to 110° C., and under a hydrogen pressure ranging from 1 to 30 atmospheres. The 2-stage reaction may be conducted in either the gas phase or the liquid phase.

The second stage of the two stage reaction, comprising the conversion of the saturated aldehyde to the alcohol, may utilize nickel catalysts of the type defined with respect to the 1-stage reaction. Thus, 2,3-dimethylbutanal may be converted to 2,3-dimethylbutanol in the presence of a nickel catalyst ranging in amount from 2 to 15% by weight of the saturated aldehyde, depending upon the nickel content of the catalyst. This second stage reaction may proceed without a solvent, at a temperature ranging from 90° to 160° C., and a hydrogen pressure of from 50 to 150 atmospheres, the exact temperature and pressure dependent upon the activity of the catalyst.

Before the saturated alcohol may be further processed in accordance with the present invention, purification of the crude product obtained by the above hydrogenation reaction is necessary. Thus, the reaction product is distilled to remove higher boiling point components, and any catalyst residue that may be present. Distillation is easily conducted at a reduced pressure ranging from 50 to 300 mm Hg.

The next step of the present process comprises the dehydration of the saturated alcohol to form the olefin mixture of 2,3-dimethylbutene-1 and 2,3-dimethylbutene-2. Dehydration is conducted with a catalyst selected from a variety of suitable catalysts such as oxalic acid, acetic anhydride, sulfuric acid, and aluminum oxide. Reaction conditions such as temperature and time may be correspondingly varied within wide limits. This dehydration reaction, however, results in the formation of by-products attributable to the rearrangement of the carbon skeleton by the dehydration catalysts. These by-products frequently comprise isomeric $C_6$ olefins which cannot be separated from one another by distillation due to the small differences in the boiling points of the individual isomers. In a preferred embodiment, the dehydration reaction may be conducted with a catalyst containing aluminum oxide, and at a temperature ranging from 260° to 320° C.

The dehydration reaction is best conducted to favor the formation of large amounts of 2,3-dimethylbutene-2, by allowing the 2,3-dimethylbutanol to flow over the dehydration catalyst at the lowest possible flow velocity. This nonetheless, results in the formation of isomeric methylpentenes, due to the rearrangement of the carbon skeleton, discussed above. Preferably, the formation of 2,3-dimethylbutene-2 from the saturated alcohol, is conducted in two stages.

In the first stage, the dimethylbutanol is circulated past the catalyst at a flow velocity of from 0.25 to 1.50 and preferably about 1.0 volumes of dimethylbutanol per volume of catalyst and per hour, which measurement may also be expressed in the notation V/V.h. The second stage comprises the isomerization of the predominantly formed 2,3-dimethylbutene-1 to the final product.

The isomerization is carried out in a known manner in the presence of acid or base catalysts. Suitable catalysts include mineral acids, oxides of aluminum, chromium or cobalt, hydroxides of sodium or potassium, alkali metals, organo metallic compounds, and hydrogenation or dehydrogenation catalysts. Sulfuric acids has proved particularly suitable for this isomerization, and may be utilized in an aqueous solution at a concentration of from 40 to 60% therein, which solution is present in an amount ranging from 10 to 50% based on the olefin mixture. The isomerization may be conducted in vacuo, as well as at the ambient pressure of reaction. In the instance where the isomerization is conducted in vacuo, the reaction is completed at the reflux temperature, which may range from 58° to 71° C. The isomerization proceeds to about 90% conversion of the olefin. The resulting reaction mixture is further processed by initial washing with bicarbonate followed by fractional distillation, and the final product, 2,3-dimethylbutene-2, is obtained. The purity of the final product may range as high as 99%.

The following examples illustrate the invention without, however, restricting it.

EXAMPLE 1

A. α-isopropylacrolein.

1,720 grams (20 moles) of isovaleraldehyde and 2,000 grams of a 30% aqueous formaldehyde solution (corresponding to 20 moles of formaldehyde) were placed in a 6 l. capacity round-bottomed flask provided with a stirrer, reflux condenser, dropping funnel and internal thermometer, and the mixture was boiled at a temperature of 76° C., with stirring and under reflux. 129 grams of di-n-butylamine was added to the mixture over a period of 10 minutes, after which the mixture was stirred for an additional 60 minutes. The mixture was continually heated during this time, and the boiling point rose to from 86° to 88° C. Heating was then discontinued, and the reaction mixture was subjected to phase separation when it reached the temperature of about 40° C. Gas chromatographic analysis of the organic phase disclosed that it contained 94% α-isopropylacrolein. The α-isopropylacrolein was thereafter separated from the higher boiling point fractions by flash distillation. 1,916 grams of a primary fraction containing 97% of α-isopropylacrolein was obtained at a temperature of 109° C., and a pressure of 760 mm Hg.

B. 2,3-dimethylbutanol.

1,000 grams of α-isopropylacrolein were hydrogenated in a steel autoclave at a temperature of 100° C. and a hydrogen pressure of 20 atmospheres. A palladium catalyst comprising 5% by weight of palladium disposed on activated charcoal, was present in an amount of 1% by weight of the unsaturated aldehyde. Hydrogenation continued until all of the hydrogen initially provided was used up, and the saturated aldehyde had been formed. At this point, the first stage of hydrogenation was complete and the palladium catalyst was exchanged for a nickel catalyst comprising approximately 57% by weight of nickel supported on kieselguhr, which nickel catalyst was introduced in an amount of 10% by weight of the aldehyde. The mixture was hydrogenated further at a temperature of 140° C. and a hydrogen pressure of 100 atmospheres. The resulting reaction product was examined by gas chromatographic analysis and was found to contain 97% of 2,3-dimethylbutanol, which was separated from the catalyst by flash distillation at a temperature of 112° C., and a pressure of 200 mm Hg.

C. 2,3-dimethylbutene-1.

The alcohol product prepared above was subjected to dehydration in the following manner. A 120 cm long reaction tube was filled with 300 ml of the dehydration catalyst γ-Al₂O₃. A 30 cm high packing of Raschig rings was arranged as a vaporization zone, approximately 80 cm above the catalyst zone. The alcohol feed stock was placed in a uniformly heated oven and heated to a temperature of 320° C., after which it was added to the top of the reaction tube by means of a metering pump, at a rate of 1.5 V/V.h (volume of alcohol per volume of catalyst and per hour). The alcohol vaporized in the Raschig ring zone and passed in aqueous form over the catalyst. A highly efficient cooler was mounted at the lower outlet of the reaction tube, and the reaction mixture condensed and dropped into a round-bottom flask that had been connected thereto to collect the condensate. After dehydration was completed, the resulting organic product was subjected to phase separation. Subsequently, the product was examined by gas chromatographic analysis, and found to contain, in addition to about 2% of the initial feed stock, 77% of 2,3-dimethylbutene-1, 17% of 2,3-dimethylbutene-2 and from 3 to 4% of isomeric C₆-olefins.

D. 2,3-dimethylbutene-2.

1,750 grams (25 ml.) of 2,3-dimethylbutene-1 and 750 grams (500 ml.) of 60% aqueous solution of sulfuric acid were placed in a 4 l. capacity round-bottomed flask provided with a stirrer, internal thermometer and reflux condenser. The reaction mixture was heated to the reflux temperature while being stirred, the temperature rising from 58° C. to 71° C. during the course of the isomerization. The reaction was continued for 30 minutes, after which time the mixture was cooled, and the sulfuric acid catalyst phase was separated. The olefinic phase was then washed with 250 grams of a saturated NaHCO₃ solution. The crude product was examined by gas chromatographic analysis and was found to contain 89% of 2,3-dimethylbutene-2, 6% of 2,3-dimethylbutene-1, and about 4 to 5% of isomeric C₆ olefins. The olefin product was further processed by fractional distillation in a column containing 36 theoretical trays. After removing the initial distillate, 1105 grams of 2,3-dimethylbutene-2 of at least 99% purity was obtained at a temperature of 74° C., and a pressure of 750 mm Hg. This yield could be increased further by recycling the initial distillate fraction.

EXAMPLE 2

A. α-isopropylacrolein.

1204 g (14 mole) of isovaleraldehyde and 1400 g of a 30% aqueous formaldehyde solution (corresponding to 14 moles of formaldehyde) were heated to 30° C. while stirring in a 5 l. capacity steel autoclave. 45 g of di-n-butylamine (0.35 mole) were then added within 30 minutes. The mixture was next heated to 100° C., and an internal pressure of 1.6 to 1.8 atmospheres was developed. After 60 minutes' reaction at 100° C., the mixture was cooled and the phases were separated. The reaction product was examined by gas chromatographic analysis, and was found to contain an average 94% of α-isopropylacrolein. The higher boiling point fractions were separated by flash distillation. A main fraction of 1361 g containing 97% of α-isopropylacrolein was obtained at a temperature of 109° C. and a pressure of 760 mm Hg.

B. 2,3-dimethylbutanol.

1,000 grams of α-isopropylacrolein prepared above were mixed with 1,000 grams of 2,3-dimethylbutanol and 10% by weight of the aldehyde of a nickel supported catalyst comprising 55% by weight of nickel on a kieselguhr support. This mixture was placed in a steel autoclave and hydrogenated at a temperature of 140° C., and a hydrogen pressure of 100 atmospheres. Upon completion of hydrogenation, the resulting reaction product was examined by gas chromatographic analysis and found to contain 98% of 2,3-dimethylbutanol, which was separable from the catalyst by flash distillation.

C. 2,3-dimethylbutene-1.

The dehydration of the alcohol formed above was carried out in a 120 cm long reaction tube filled with 300 ml of γ-Al₂O₃ provided in the form of small rods. The reaction apparatus included a 30 cm high packing of Raschig rings was arranged as a vaporization zone and located approximately 80 cm above the catalyst zone. The alcohol feed stock was placed in a uniformly heated oven and brought to a temperature of 320° C., after which it was added to the top of the apparatus by means of a metering pump at a rate of 1.5 V/V.h. The alcohol vaporized in the Raschig ring zone and passed into the gaseous state as it flowed over the catalyst. A highly efficient cooler was mounted at the lower end of the reaction tube, and caused the reaction mixture to condense and drop into a round-bottom flask that had been connected thereto.

Phase separation of the condensate was conducted, after which the organic product was examined by gas chromatographic analysis, and was found to contain 81% of 2,3-dimethylbutene-1, 11% of 2,3-dimethylbutene-2, 4% of 2,3-dimethylbutanol, and 3 to 4% of isomeric C₆-olefins.

D. 2,3-dimethylbutene-2.

400 g (570 ml) of 2,3-dimethylbutene-1 and 40 g (27 ml) of 60% sulphuric acid were placed in a glass autoclave. The mixture was then heated under its own pressure for 1 hour at 70° C. After cooling, phase separation and washing with bicarbonate, the crude product was examined and found to contain 85% of 2,3-dimethylbutene-2, 10% of 2,3-dimethylbutene-1, and 4 to 5% of isomeric C₆-olefins.

This mixture of olefins was separated by fractional distillation in a column containing 36 theoretical trays. 259 g of 2,3-dimethylbutene-2 of at least 99% purity was obtained. The yield could be increased still further by recycling the initial distillate.

What we claim is:

1. A process for preparing 2,3-dimethylbutene-2 comprising
   treating isovaleraldehyde by methylenation to form α-isopropylacrolein,
   treating α-isopropylacrolein by hydrogenation to form 2,3-dimethylbutanol,
   treating 2,3-dimethylbutanol by dehydration to form an olefin mixture, said olefin mixture including 2,3-dimethylbutene-1 and 2,3-dimethylbutene-2, and
   isomerizing the 2,3-dimethylbutene-1 of said olefin mixture to form 2,3-dimethylbutene-2.

2. The process according to claim 1, wherein said methylenation comprises reacting isovaleraldehyde with formaldehyde in the presence of a catalytic amount of an amine selected from primary amines and secondary amines.

3. The process according to claim 2, wherein said amine is secondary amine having the formula $R_1-CH_2-CH_2-NH-R_2$ wherein $R_1$ is selected from hydrogen, an alkyl radical having up to 11 carbon atoms, and a cycloaliphatic radical having from 5 to 6 carbon atoms; and $R_2$ is selected from an alkyl radical having up to 13 carbon atoms, and a cycloaliphatic radical having from 5 to 6 carbon atoms.

4. The process according to claims 2 or 3, wherein said methylenation is conducted at a temperature of from 60° to 120° C., and under a pressure prevailing at said temperature.

5. The process according to claim 1, wherein said hydrogenation is conducted in two stages comprising a first stage of reacting α-isopropylacrolein in the presence of hydrogen and a noble metal catalyst to form 2,3-dimethylbutanal, and a second stage of reacting 2,3-dimethylbutanal with hydrogen and a nickel catalyst to form 2,3-dimethylbutanol.

6. The process according to claim 5 wherein said first stage is conducted at a temperature of from 80° to 130° C., and a hydrogen pressure of from 1 to 30 atmospheres, and said noble metal catalyst contains palladium, and said second stage is conducted at a temperature of from 90° to 160° C., and a hydrogen pressure of from 50 to 150 atmospheres.

7. The process according to claims 5 or 6 wherein said noble metal catalyst is present in an amount of from 0.1 to 2% by weight of said α-isopropylacrolein, and said nickel catalyst is present in an amount of from 2 to 15% by weight of said 2,3-dimethylbutanal.

8. The process according to claim 1, wherein said hydrogenation is conducted in one stage in the presence of a nickel catalyst.

9. The process according to claims 1 or 8, wherein said hydrogenation is conducted at a temperature of from 90° to 160° C., and a hydrogen pressure of from 50 to 150 atmospheres.

10. The process according to claim 8, wherein a nickel catalysts are present in an amount of from 2 to 15% by weight of said α-isopropylacrolein.

11. The process according to claims 1 or 10, wherein intermediate said hydrogenation and said dehydration, said 2,3-dimethylbutanol is subjected to distillation.

12. The process according to claim 11, wherein said distillation is conducted at a pressure of 50 to 300 mm Hg.

13. The process according to claim 1, wherein said dehydration comprises circulating said 2,3-dimethylbutanol past a dehydration catalyst at a flow velocity of from 0.25 to 1.50 volumes of dimethylbutanol per volume of catalyst and per hour.

14. The process according to claim 13, wherein said dehydration catalyst is selected from oxalic acid, acetic anhydride, sulfuric acid and aluminum oxide.

15. The process according to claim 14, wherein said catalyst comprises an aluminum oxide catalyst.

16. The process according to claims 14 or 15, wherein said dehydration is conducted at a temperature of from 260° to 320° C.

17. The process according to claim 1, wherein said isomerizing takes place in the presence of an isomerization catalyst selected from acid catalysts and base catalysts.

18. The process according to claim 17, wherein said isomerization catalyst comprises an aqueous solution of sulfuric acid.

19. The process according to claim 18, wherein said sulfuric acid solution is prepared in a concentration ranging from 40 to 60%, and is utilized in an amount of from 10 to 50% of said 2,3-dimethylbutene-1.

* * * * *